United States Patent [19]

Smitherman

[11] Patent Number: 5,015,467

[45] Date of Patent: May 14, 1991

[54] COMBINED ANTICALCULUS AND ANTIPLAQUE COMPOSITIONS

[75] Inventor: Herbert C. Smitherman, Cincinnati, Ohio

[73] Assignee: The Procter & Gamble Company, Cincinnati, Ohio

[21] Appl. No.: 543,594

[22] Filed: Jun. 26, 1990

[51] Int. Cl.$^5$ .................. A61K 7/18; A61K 7/24; A61K 9/68

[52] U.S. Cl. .................. 424/52; 424/48; 424/49; 424/55; 424/435; 424/440; 424/441; 426/3

[58] Field of Search .................. 424/48, 49, 55, 52, 424/435, 440, 441; 426/3

[56] References Cited

U.S. PATENT DOCUMENTS

| | | | |
|---|---|---|---|
| 4,452,820 | 6/1984 | D'Amelia et al. | 426/3 |
| 4,582,709 | 4/1986 | Peters et al. | 426/74 |
| 4,663,071 | 5/1987 | Bush et al. | 252/174.19 |
| 4,689,167 | 8/1987 | Collins et al. | 252/95 |
| 4,721,580 | 1/1988 | Gosselink | 252/90 |
| 4,877,896 | 10/1989 | Maldonado et al. | 560/14 |
| 4,904,824 | 2/1990 | Horng et al. | 562/583 |
| 4,925,586 | 5/1990 | Baker et al. | 252/90 |
| 4,959,409 | 9/1990 | Heinzman et al. | 525/61 |
| 4,968,451 | 11/1990 | Scheibel et al. | 252/549 |

*Primary Examiner*—Shep K. Rose
*Attorney, Agent, or Firm*—Jerry J. Yetter; Richard C. Witte; Douglas C. Mohl

[57] ABSTRACT

Tartrate monosuccinate and tartrate disuccinate compounds of the formulae $HO(CHCOOX)CH(COOX)OCH(COOX)CH_2COOX$ and $CH_2(COOX)CH(COOX)O(CH[COOX])_2OCH(COOX)CH_2COOX$ are used in combination with various polymers to provide anticalculus and antiplaque effects on teeth. Oral care compositions such as dentifrices, mouthwashes, and the like, are provided. Use of the tartate-succinates and polymers in combination with other oral car ingredients such as fluoride, pyrophosphate and antibacterials is also described.

12 Claims, No Drawings

COMBINED ANTICALCULUS AND ANTIPLAQUE COMPOSITIONS

TECHNICAL FIELD

The present invention relates to oral care compositions such as dentifrices, mouthwashes, lozenges, chewing gums, and the like, which are designed to prevent the accumulation of calculus, or "tartar", as it is sometimes called, on teeth, while concurrently preventing plaque.

BACKGROUND OF THE INVENTION

Dental calculus is a deposit which forms on the surfaces of the teeth at the gingival margin. Supragingival calculus appears principally in the areas near the orifices of the salivary ducts; e.g., on the lingual surfaces of the lower anterior teeth, on the buccal surfaces of the upper first and second molars, and on the distal surfaces of the posterior molars.

Mature calculus consists of an inorganic material which is largely calcium phosphate arranged in a hydroxyapatite crystal lattice structure similar to bone, enamel and dentin. An organic portion is also present and consists of desquamated epithelial cells, leukocytes, salivary sediment, food debris and various types of microorganisms.

As the mature calculus develops, it becomes visibly white or yellowish in color unless stained or discolored by some extraneous agent. In addition to being unsightly and undesirable from an aesthetic standpoint, the mature calculus deposits are constant sources of irritation of the gingiva.

A wide variety of chemical and biological agents have been suggested in the art to retard calculus formation or to remove calculus after it is formed. Mechanical removal of this material periodically by the dentist is, of course, routine dental office procedure.

The chemical approach to calculus inhibition generally involves chelation of calcium ion and/or crystal growth inhibition which prevents the calculus from forming and/or breaks down mature calculus by removing calcium.

Dental plaque is a combination of minerals and bacteria. The bacteria associated with plaque can cause inflammatory gingivitis. Gingivitis, in turn, may lead to periodontitis, and, ultimately, tooth loss. Therefore, it would be highly desirable to develop compositions and methods for inhibiting plaque.

Since plaque can develop and adhere most easily at relatively irregular surfaces, such as those afforded by calculus, it would be of particular advantage to concurrently attack both the calculus and the plaque problems. The extensive literature in this area bespeaks the ongoing attempts of scientists and dentists to address the dual problems of dental calculus and dental plaque.

It is an object of the present invention to provide combined calculus and plaque control. The present invention employs novel combinations of anti-calculus and anti-plaque ingredients which concurrently afford the desired benefits.

BACKGROUND ART

PLAQUE: Numerous compositions and methods for inhibiting the formation of plaque are reported in the literature.

U.S. Pat. No. 4,847,070, issued July 11, 1989, to Pyrz et al., discloses oral compositions which are effective against calculus containing a chelating agent which is an acrylic acid polymer or copolymer or EDTA, a strontium ion source, a fluoride ion source, a pyrophosphate ion source, and a pharmaceutically acceptable carrier. The mass average molecular weight of the acrylic acid polymer or copolymer used is in the range of about 1,000 to about 1,200,000.

U.S. Pat. No. 4,816,245, issued Mar. 28, 1989, to Gaffar, discloses a method of inhibiting human dental plaque and gingivitis involving regular application to the oral cavity of an oral composition containing an effective plaque- and gingivitis-inhibiting amount of polyvinyl phosphonic acid, or salt thereof, having a number average molecular weight of about 4,000 to 9,100.

U.S. Pat. No. 4,775,525, issued Oct. 4, 1988, to Pera, discloses a dental treatment composition and method for reducing dental plaque. The disclosed method comprises treating dental surfaces with a composition containing sodium alginate, which acts as a calcium ion chelating agent which weakens the bond between the plaque and the teeth, thereby allowing easy removal of the plaque by subsequent brushing. The compositions disclosed in this patent may also contain benzalkonium chloride and zinc sulfate, which provide for desensitizing the teeth and eliminating halitosis.

U.S. Pat. No. 4,759,925, issued July 26, 1988, to Gaffar et al., discloses the use of a mixture of certain perfluoroalkyl surfactants and an alkali metal or ammonium cation as a dentifrice or a mouthwash to prevent plaque formation.

U.S. Pat. No. 4,627,977, issued Dec. 9, 1986, to Gaffar et al., discloses an oral composition containing a calculus-inhibiting amount of a linear molecularly dehydrated polyphosphate salt and, to inhibit enzymatic hydrolysis of said polyphosphate salt in saliva, a combination of a fluoride ion-providing source and a synthetic anionic linear polymeric polycarboxylate.

U.S. Pat. No. 4,528,179, issued July 9, 1985, to Gaffar, discloses a method of inhibiting human dental plaque and gingivitis by the regular application to the oral cavity of an oral composition containing an effective plaque- and gingivitis-inhibiting amount of polyvinyl phosphonic acid or salt thereof. The polyvinyl phosphonic acid of this reference has a preferred number average molecular weight of about 6,000 to about 100,000.

U.S. Pat. No. 4,428,930, issued Jan. 31, 1984, to Chang, discloses a dentifrice composition containing a water-dispersible, membrane-forming material which, when applied to tooth surfaces in an oral environment, attaches thereto and forms a substantially continuous hydrophobic barrier thereon, which hydrophobic barrier substantially reduces elution of a previously applied therapeutic agent. This patent also discloses a method for inhibiting plaque formation on teeth which comprises contacting the teeth with an effective amount of the above-described composition. Polymeric anionic membrane forming materials disclosed as useful in the compositions of this patent include a class of polymers having a polyolefinic main chain with acid functionalities pendent therefrom. Typical of the materials which can comprise the pololefinic main chain are polymers of ethylene, propylene, styrene, unsaturated carboxylic acids, and copolymers of two or more of these materials. Representative polymeric anionic membrane forming materials disclosed as useful in the compositions of this patent include polyacrylic acid having a molecular weight in the range of 2,000 to 4,000,000; sodium polystyrenesulfonate having a molecular weight in the range of about 5,000 to 6,000,000; "GANTREZ AN", available from GAF corporation; polyvinyl phosphate; and copolymers of acrylates which contain pendent carboxyl groups.

U.S. Pat. No. 4,375,461, issued Mar. 1, 1983, to Gander et al., discloses compositions and methods for preventing the attachment of dental plaque to the surfaces of the teeth of mammals. These disclosed compositions and methods comprise certain sulfonated vinylaromatic homopolymers and copolymers and the pharmaceutically acceptable salts thereof in a pharmaceutically acceptable vehicle, and a periodic application thereof to teeth. Hydrophilic polymeric anionic sulfates useful for dental plaque control in accordance with the disclosure of this patent are essentially sulfonated homopolymers of both unsubstituted and substituted styrene, 1-vinylnaphthalene, 2-vinylnaphthalene, and acenaphthylene, and certain copolymers thereof. Representative examples of vinyl aromatic monomers, homopolymers, and copolymers which are available in commerce and can be converted to the hydrophilic polymeric sulfonates of this patent are the following: (a) polystyrene and sodium polystyrene sulfonate of varying molecular weights available from Pressure Chemical Company; (b) styrene/butadiene (85/15) copolymer; (c) styrene/isobutylene (60/40) copolymer; (d) vinylbenzyl chloride monomer, 60/40 meta-/paraisomers, available from Dow Chemical Company; and (e) halostyrene monomers available from Polysciences Inc., and Aldrich Chemical Company.

U.S. Pat. No. 4,362,713, issued Dec. 7, 1982, to Buck, discloses compositions and methods for preventing the attachment of dental plaque to the teeth of mammals. The disclosed compositions and methods comprise certain salts of certain maleic acid copolymers in a pharmaceutically acceptable vehicle and the periodic application thereof to teeth. This patent further discloses that certain hydrophilic alkali metal and ammonium salts of 1:1 copolymers of styrene and maleic acid and 1:1 copolymers of certain linear 1-alkenes and maleic acid have been found to inhibit the deposition of dental plaque onto human teeth when applied thereon.

U.S. Pat. No. 4,224,309, issued Sept. 23, 1980, to Gaffar et al., discloses an oral composition containing an antibacterial antiplaque agent and an anti-stain additive which reduces staining caused by the antibacterial antiplaque agent, without substantially diminishing the activity of the antibacterial antiplaque agent. Bisbiguanido hexanes, such as chlorhexidine and alexidene, and quaternary ammonium salts, such as benzethonium chloride and cetyl pyridium chloride, are typical examples of antibacterial agents. The anti-stain additive is 2-phosphonobutane-1,2,4-tricarboxylic acid or an orally acceptable salt thereof.

U.S. Pat. No. 4,138,477, issued Feb. 6, 1979, to Gaffar, discloses a composition which is useful for the prevention and control of mouth odor and is also effective in preventing calculus, plaque, caries and periodontal disease. This composition contains, as its essential agent, a zinc-polymer combination formed by the reaction or interaction of a zinc compound with an anionic polymer containing carboxylic, sulfonic and/or phosphonic acid radicals.

U.S. Pat. No. 4,118,474, issued Oct. 3, 1978, to Gaffar et al., discloses an antibacterial oral composition effective at promoting oral hygiene which contains an antibacterial antiplaque agent and an additive for reducing staining of dental surfaces without substantially diminishing the activity of the antibacterial and antiplaque agent. Bisbiguanido hexanes, such as chlorhexidine and alexidine, and quaternary ammonium salts, such as benzethonium chloride and cetyl pyridinium chloride, are typical examples of antibacterial antiplaque agents. The anti-stain additive is phosphonoacetic acid or salts thereof.

U.S. Pat. No. 4,118,473, issued Oct. 3, 1978, to Gaffar et al., discloses an antibacterial oral composition effective to promote oral hygiene which contains an antibacterial antiplaque agent and an additive for reducing staining of dental surfaces without substantially diminishing the activity of the antibacterial and antiplaque agent. Bis-biguanido hexanes, such as chlorhexidine and alexidine, and quaternary ammonium salts, such as benzethonium chloride and cetyl pyridinium chloride, are typical examples of antibacterial antiplaque agents. The antistain additive is an N-methylene phosphonate compound, such as iminodiacetic N-methylene phosphonic acid and salts thereof.

United Kingdom Patent Application 2151478-A, published July 24, 1985, assigned to the Colgate-Palmolive Company, discloses that dental plaque and gingivitis are inhibited by the regular application to the oral cavity of an oral composition containing an effective plaque- and gingivitis-inhibiting amount of polyvinyl phosphonic acid or a salt thereof. The polyvinyl phosphonic acid, and salt thereof, have a preferred number average molecular weight of from about 6,000 to 100,000.

CALCULUS: Numerous compositions and methods for inhibiting the formation of calculus are reported in the literature.

U.S. Pat. No. 4,885,155, to Parran and Sakkab, granted Dec. 5, 1989, relates to oral compositions containing pyrophosphate salts which provide an anticalculus benefit.

British Patent No. 490,384, Feb. 15, 1937, discloses oral compositions containing ethylenediaminetetraacetic acid, nitrilotriacetic acid and related compounds as anticalculus agents.

U.S. Pat. No. 3,678,154, July 18, 1972 to Widder, et al. discloses oral compositions containing certain polyphosphonates and fluoride. U.S. Pat. No. 3,737,533, June 5, 1973 to Francis discloses oral compositions containing certain carbonyl diphosphonates.

In addition to the above references, the prior art discloses dentifrices and mouthwashes containing soluble pyrophosphate salts which have been indicated for a variety of purposes. Included among such references are U.S. Pat. No. 2,941,926, June 21, 1960 to Salzmann, et al. which discloses dental powders containing chlorophyll and pyrophosphate salts. U.S. Pat. No. 3,137,632, June 16, 1964 to Schiraldi discloses toothpastes containing pyrophosphate salts. U.S. Pat. Nos. 3,927,201 and 3,927,202, Dec. 16, 1975 to Baines, et al. and Harvey, et al., respectively, disclose toothpastes which utilize soluble pyrophosphates as abrasives. U.S. Pat. No. 4,244,931, Jan. 13, 1981 and 4,247,5226, Jan. 27, 1981 to Jarvis, et al. disclose pyrophosphate salts in dicalcium phosphate systems. Japanese Patent Application Disclosure No. 4945-1974 discloses soluble pyrophosphates in a variety of dentifrice systems. U.S. Pat. No. 4,333,551, Apr. 6, 1982 to Parran discloses tetraalkali metal salts in mouthwash compositions. Draus, Lesniewski and Miklos, Pyrophosphate and Hexametaphosphate Effects in Vitro Calculus Formation, Arch. Oral Biol., Vol. 15, pp. 893-896 (1970), disclose the in vitro effectiveness of soluble pyrophosphate salts against calculus. However, they indicate that pyrophosphate efficacy would be inhibited by phosphatases in vivo.

The references suggesting that pyrophosphates could reduce calculus, but either suggesting problems associated with their use or not recognizing problems, are Rapp, G. W. et al., "Pyrophosphate: a factor in Tooth Erosion", J. D. Res. March-April 1960, Vol. 39, No. 2 pp. 372-376; the Draus article cited above; Briner et al., "In Vitro and In Vivo Evaluation of Anticalculus Agents", Calc. Tiss. 11, pp. 10-22 (1973); U.S. Pat. No. 3,934,002, Jan. 20, 1976 to Haefele; and British Patent No. 490,384, Feb. 15, 1937.

U.S. Pat. No. 4,847,070, July 11, 1989 to Pyrz et al. relates to oral compositions which are effective against calculus containing a chelating agent which is an acrylic acid polymer or copolymer or EDTA, together with a strontium source, a fluoride ion source and a pyrophosphate ion source.

U.S. Pat. No. 4,661,341, Apr. 28, 1987 to Benedict et al. relates to oral compositions containing an anticalculus agent which is an acrylic acid polymer or copolymer.

U.S. Pat. No. 4,022,880, May 10, 1977 to Vinson et al. relates to compositions for inhibiting dental plaque and calculus formation comprising zinc ions and a nontoxic, organoleptically acceptable antibacterial agent.

U.K. Patent Application GB 2,200,551, Gaffar, Nabi and Jannone, filed Jan. 27, 1988, published Aug. 10, 1938, relates to antibacterial antiplaque and anticalculus oral compositions containing a linear molecularly dehydrated polyphosphate salt and a noncationic antibacterial agent.

U.S. Pat. No. 4,656,031, Apr. 7, 1987 to Lane et al. relates to a dentifrice which includes a surfactant and an antiplaque agent comprising a substantially water-insoluble noncationic antimicrobial agent or a zinc salt or a mixture thereof.

European Patent Application 0,251,591, Jackson et al., filed June 19, 1987 relates to oral hygiene compositions comprising specified pyrophosphates and antibacterials.

The synthesis of tartrate monosuccinate and tartrate disuccinate compounds of the type used in the practice of this invention is disclosed in U.S. Pat. No. 4,663,071, to Bush, Connor, Heinzman and Mackey, granted May 5, 1987.

All of the foregoing patents and publications are incorporated herein by reference.

SUMMARY OF THE INVENTION

The present invention encompasses oral care composition, comprising:

a) An effective amount of an anticalculus agent which is a member selected from the group consisting of the acid or salt form of tartrate monosuccinate, tartrate disuccinate, and mixtures thereof;

b) An effective amount of a plaque-inhibiting polymer; and c) A toxicologically acceptable oral carrier.

Typical oral care compositions herein comprise at least about 0.1%, generally from about 1% to about 15%, by weight of said anticalculus agent. Preferred oral care compositions, herein are those wherein said anticalculus agent is a mixture of said tartrate monosuccinate and tartrate disuccinate at a weight ratio of tartrate monosuccinate: tartrate disuccinate from about 20:80 to about 80:20, most preferably at a weight ratio of about 40:60.

In the oral care compositions herein, non-limiting examples of the plaque-inhibiting polymer comprise members selected from the group consisting of carboxy starch polymers (preferred), acrylic acid polymers, phosphoric acid polymers, maleic acid polymers, sulfonated polymers, and mixtures thereof, and other polypeptides, as well as modified forms of such polymers, e.g., zinc-anionic polymer combinations, and mixtures thereof. As noted, the preferred polymers herein are poly-anionic. Typical compositions herein comprise an effective amount, i.e., at least about 0.1% by weight of said polymer, generally from about 0.1% to about 5.0% by weight of said polymer, or polymer mixtures. Higher levels, e.g., 15%, can be used, if desired.

It will be appreciated that oral care compositions according to this invention include, but are not limited to, those the oral carrier comprises a dentifrice, mouthwash, lozenge or chewing gum.

It will also be appreciated that oral care compositions according to this invention can also, optionally, comprise an effective amount of various oral care adjuvants, especially those which are members selected for the group consisting of:

i) fluoride ion sources;
ii) antibacterial agents;
iii) sodium and potassium nitrates;
iv) sources of zinc, indium, strontium or stannous cations;
v) peroxides;
vi) chelants and sequestrants selected from various phosphates, and EDTA; and
vii) mixtures of adjuvants i through vi.

Typical anti-calculus, anti-plaque and anti-caries compositions will, for example, contain a fluoride ion source such as those selected from sodium fluoride, sodium mono-fluorophosphate and stannous fluoride. Antibacterial agents such as TRICLOSAN (5-chloro-2-(2,4-dichlorophenoxy)phenol, also known as 2,4,4'-trichloro-2'-hydroxydiphenyl ether; see U.S. Pat. No. 3,506,720) can advantageously be used in the present compositions to further control plaque and gingivitis. Such examples of adjuvants are given here by way of example, and not for purposes of limitation.

The present invention also encompasses a method for preventing the accumulation of calculus on dental enamel while concurrently inhibiting plaque formation on (or adherence to) said enamel, comprising contacting said enamel with a safe and effective amount of a composition as disclosed herein. Such methods can be carried out in conjunction with the use of various adjunct oral care ingredients, as described in more detail hereinafter.

All percentages, ratios and proportions herein are by weight, unless otherwise specified.

DETAILED DESCRIPTION OF THE INVENTION

I. TMS/TDS: The present invention employs tartrate monosuccinate and tartrate disuccinate materials of the following formulae:

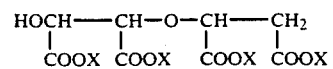

i.e., tartrate monosuccinate, otherwise designated "TMS"; and

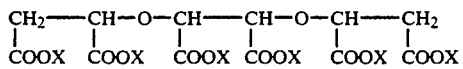

i.e., tartrate disuccinate, otherwise designated "TDS", and wherein X in the above formulae can be, for example, H or a salt-forming cation, especially cations which form water-soluble salts, e.g., alkali metal, ammonium, alkylammonium, alkanolammonium, and the like. Sodium and potassium cations are conveniently and economically used to form salts of TMS and TDS for use in this invention.

The TMS and TDS materials can be prepared using the procedures disclosed in U.S. Pat. No. 4,663,071, cited above, using maleates and tartrates in whatever isomeric forms are convenient to the formulator, e.g., D-, L- or DL stereoisomers of tartaric acid. In general, mixtures of TMS and TDS are secured, which, if desired, can be separated into their individual components, e.g., by HPLC. As noted, mixtures of TMS and TDS are perfectly acceptable for use herein.

Reaction A - An alternate mode for preparing mixtures of TMS/TDS having a desirably higher proportion of TDS is as follows. The reaction illustrated employs water (122 g.), 50% aq. NaOH (608 g.), L-tartaric acid (150 g.), Ca(OH)z (118 g.) and maleic anhydride (392 g.).

The water is added to the reaction vessel which is placed in a water bath at 60° C. The NaOH is added with slow stirring. The L-tartaric acid is added slowly and allowed to dissolve. The exotherm is maintained at 60°–80° C. Slowly add the $Ca(OH)_2$ to form a milky suspension. Maleic anhydride is slowly added while keeping the reaction temperature $\leq 85°$ C. The mixture is allowed to react at 70°–80° C. for 1 hour during which time it will turn from a chalky white suspension to a honey colored viscous reaction mixture. After 1 hour, the reaction temperature is lowered to 30° C. and maintained for a total reaction duration of 9–10 days. The reaction concentration is maintained at 60% sodium organic salts. The reaction is monitored by HPLC to determine the optimum yield. (Stir the reaction about 0.5 hour before sampling.) When the yield of TMS +TDS approaches a plateau, the reaction is quenched with ca. 1400 g $H_2O$ and by removing the calcium.

Calcium removal is as follows. Heat the reaction solution to 70° C. with stirring. Slowly add 161 g $Na_2CO_3$ followed by 31.9 g of $NaHCO_3$. Rinse with extra $H_2O$ if needed. Stir the mixture at 70° C., pH 10, for 4 hours. After 4 hours, cool to $\leq 35°$ C. and filter through coarse fritted filters. Rinse with minimal $H_2O$.

Acid workup is as follows. Add about 450 g of 50% $H_2SO_4$ to the "calcium free" solution to pH 4 with stirring to precipitate the residual maleate. Maintain the exotherm at $\leq 50°$ C. Let the solution sit overnight to enhance crystallization. Filter through coarse fritted filters via vacuum filter flasks. Use no rinse. Slowly add 160 g of 50% NaOH to the filtrate to pH 9 with stirring. Maintain the exotherm at $\leq 50°$ C. Concentrate the solution to about half the current volume (to precipitate $Na_2SO_4$) and let sit overnight to enhance crystallization. Filter off the $Na_2SO_4$ through coarse fritted filters via vacuum filter flasks. Repeat the evaporation and filtration as often as necessary to remove residual $Na_2SO_4$.

Workup in alcohol is as follows. Slowly pour the reaction solution (~40% concentration) into 8.8 L of stirring methanol (MeOH) to remove residual maleate, fumarate, carbonate, and sulfate. The TMS/TDS will precipitate out on the bottom of the vessel as a sticky "gum", while the impurities will remain in the MeOH/$H_2O$ layer. Decant/Siphon off as much of the MeOH/$H_2O$ as possible and discard. Redissolve the TMS/TDS with 1.6 L $H_2O$ using heat and stirring as necessary. Cool to $\leq 35°$ C. and repeat with a second extraction. Pour the solution into 6.4 L of stirring MeOH. Again decant/siphon off as much of the MeOH/$H_2O$ as possible and discard. Redissolve the TMS/TDS in 1.4 L water and repeat as before, using 5.6 L methanol. Redissolve the TMS/TDS in ca. 1 L $H_2O$. It is now ready for the final workup.

Final workup is as follows. Adjust the reaction solution to about pH 8.5 at 24° C. Heat to ca. 80° C. with stirring and nitrogen sparging to remove residual traces of MeOH. Concentrate the solution to 35% sodium organic salts. Cool to room temperature. Adjust the solution to the desired pH. Add $H_2O$ to adjust the final concentration if necessary. Filter through medium fritted filters.

Reaction B - Another, somewhat simpler, procedure which can be employed to prepare TMS/TDS mixtures comprising a higher ratio of TDS to TMS is as follows. The reaction illustrated employs water (86 g.), 50% NaOH (336 g.), L-tartaric acid (150g.) $Ca(OH)_2$ (89 g.) and maleic anhydride (196 g.).

Add $H_2O$ to the reaction vessel which is placed in a water bath at 60° C. Add the NaOH with slow stirring. Slowly add the L-tartaric acid and let dissolve. Maintain the exotherm at 60°–80° C. Slowly add $Ca(OH)_2$ which will form a milky suspension. Slowly add maleic anhydride while keeping the reaction temperature $\leq 85°$ C. Allow the mixture to react at 70°–80° C. for 1 hour during which time it will turn from a chalky white suspension to a honey colored viscous reaction mixture. After 1 hour, lower the reaction temperature to 30° C. and maintain it for a total reaction duration of 9–10 days. Maintain the reaction concentration at 60% sodium organic salts. Monitor the reaction by HPLC to determine the optimum yield. (Stir the reaction mixture about 0.5 hour before sampling.) When the yield of TMS +TDS approaches a plateau, proceed by quenching the reaction with ca. 850 g. $H_2O$ and by removing the calcium.

Calcium removal is as follows. Heat the reaction solution to 70° C. with stirring. Slowly add 121.9 g. $Na_2CO_3$ followed by 24.4 g. $NaHCO_3$ to form a milky suspension. The mole ratio of carbonate to calcium is 1.2 carbonate to 1.0 calcium. Adjust the pH of the suspension to 10.0 at 70° C. with additional $Na_2CO_3$ or $NaHCO_3$ if needed. Rinse with extra $H_2O$ if needed. Stir the mixture at 70° C., pH 10, for 4 hours. After 4 hours, cool to $\leq 35°$ C. and filter through coarse fritted filters. Rinse with minimal $H_2O$.

Workup with methanol is optional. If methanol (MeOH) workup is used, the procedure is the same as in Reaction A, above.

Final workup is as follows. If a MeOH workup is used, adjust the reaction solution to about pH 8.5 at 24° C. Heat to ca. 80° C. with stirring and nitrogen sparging to remove residual traces of MeOH. Concentrate the solution to 35% sodium organic salts. Cool to room temperature. Adjust the solution to the desired pH. Add $H_2O$ to adjust the final concentration if necessary. Filter through medium fritted filters.

II. POLYMERS: A variety of polymers can be used to control plaque formation on, or adherence to, dental enamel. (It will be appreciated that the term "plaque-inhibiting polymer", as used herein, is intended to encompass polymers which function either by removing plaque or, more likely, by presenting a surface on the dental enamel to which the plaque does not readily adhere, i.e., "anti-adherent" polymers. Whatever the mode of action, the desired plaque-inhibiting, or "anti-plaque", result is secured. The following listing of polymers useful herein is by way of illustration and not limitation.

1. Polyvinyl phosphoric acid polymers in the 4000, and above, molecular weight range. See U.S. Pat. No. 4,816,245 and U.K. 2151478A.
2. Polyacrylic, polystyrenesulfonate, and acrylate copolymers, especially of the GANTREZ AN series. See U.S. Pat. No. 4,428,930.
3. Sulfonated vinylaromatic homopolymers and copolymers. See U.S. Pat. No. 4,375,461.
4. Maleic acid copolymers. See U.S. Pat. No. 4,362,713.
5. Zinc-polymer (anionic) combinations. See U.S. Pat. No. 4,118,474.
6. Preferred polymers for use herein comprise the class of carboxy starch polymers of the formulae:

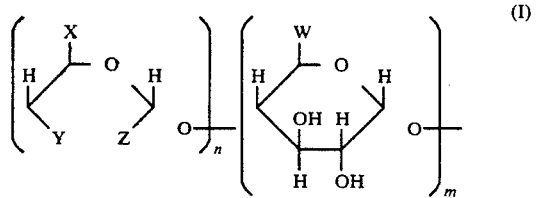

(I)

wherein W and X are independently selected from $CH_2OH$, $CHO$ and $CO_2H$, preferably from $CH_2OH$ and $CO_2H$, or the neutralized carboxylic acid salts thereof, Y and Z are independently selected from $CHO$ and $CO_2H$, or the neutralized carboxylic acid salts thereof, n is in the range of from about 5 to about 2500, preferably from about 5 to about 1500, most preferably from about 5 to about 1000, m is in the range of from 0 to about 2500, preferably from 0 to about 1500, most preferably from 0 to about 1000, provided that the sum of n and m ranges from about 5 to about 2500, preferably from about 5 to about 1500, most preferably from about 5 to about 1000. The degree of carboxylation of the carboxy starch polymer typically ranges from about to about 3, preferably from about 1.5 to about 3, most preferably from about 1.7 to about 3. The phrase "degree of carboxylation" is defined as the number average of carboxy groups per starch monomer contained in the polymer chain. The term "monomer" refers to the individual starch groups having either the n or m subscript, and not the two-monomer structure shown as compound I. The mass average molecular weight of the carboxy starch polymer typically ranges from about 1,000 to about 500,000, preferably from about 1,000 to about 300,000.

Such polymers used in the present invention may comprise repeating units of the two-monomer block shown as structure I, it may comprise a block copolymer, such as when a long chain of the monomer having the n subscript is joined with a long chain of the monomer having the m subscript, it may comprise a random mixture of the individual monomers of the two-monomer block shown as structure I, or it may comprise solely the monomer having the n subscript, as when m is zero, of the two-monomer block shown as structure I.

The carboxy starches used in the present invention are typically prepared by the oxidation of a dialdehyde starch. The dialdehyde starch may be obtained through the procedure disclosed in "Methods in Carbohydrate Chemistry" Volume IV, page 316, the disclosure of which is incorporated herein by reference. In this procedure, a solution containing sodium metaperiodate and water is added to a stirred suspension containing starch and water. The resulting mixture is stirred at room temperature for a period of time, and the solid dialdehyde starch product is isolated by filtration and dried.

The dialdehyde starch is typically converted to the desired carboxy starch polymer by oxidation with either chlorous acid, as shown in U.S. Pat. No. 3,784,475, issued Jan. 8, 1974, to Diehl, the disclosure of which is incorporated herein by reference, or with dinitrogen tetroxide, as shown in U.S. Pat. No. 3,665,000, issued May 23, 1972, to Hills, the disclosure of which is incorporated herein by reference.

In a typical chlorous acid oxidation, dialdehyde starch is added to an aqueous solution containing sodium chlorite and acetic acid. The mixture is stirred at room temperature for a period of time. Air is then bubbled through the mixture until a clear solution is obtained and the pH is adjusted using a sodium hydroxide solution. The reaction mixture is then poured onto ethanol to precipitate the product, which is isolated by filtration and dried.

In a typical dinitrogen tetraoxide oxidation, a reaction vessel is charged with a solution of dinitrogen tetroxide in methylene chloride at low temperatures. The solution is stirred vigorously as dialdehyde starch is added, and the mixture is allowed to warm to room temperature with stirring. After a period of time, additional dinitrogen tetraoxide is added, and stirring is continued. Argon gas is bubbled through the reaction mixture to remove nitrous oxide. The white solid product is then filtered, washed with water, and dried.

Preferred starch polymers useful in the present invention are of the general formulas:

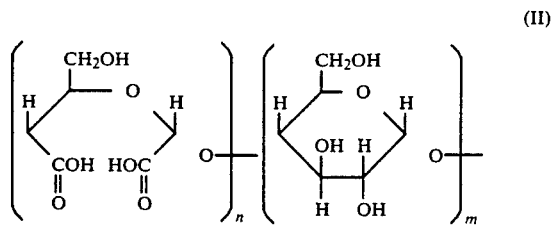

(II)

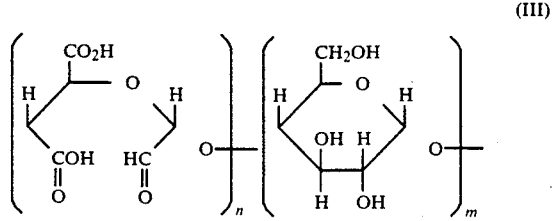

(III)

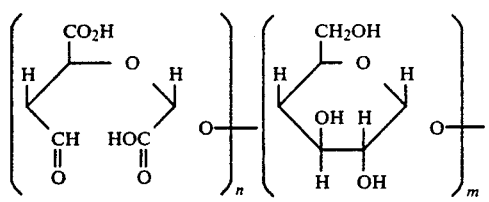

(IV)

or the neutralized carboxylic acid salts thereof, wherein n and m are as hereinbefore defined. The number average degree of carboxylation of these preferred starch polymers typically is in the range of from about 1 to about 2.5, more typically from about 1.5 to about 2, most typically from about 1.5 to about 1.9. The mass average molecular weight of these preferred starch polymers is typically in the range of from about 1,000 to about 500,000, preferably from about 4,000 to about 250,000, most preferably from about 50,000 to about 250,000.

These preferred starch polymers may be prepared by the methods disclosed in "Chlorous Acid Oxidation of Periodate Oxidized Cornstarch", B. T. Hofreiter, I. A. Wolff and C. L. Mehltretter, J. Amer. Chem Soc.. 79, 6457 (1957), the disclosure of which is incorporated herein by reference.

Individually, these preferred carboxy starch polymers may comprise repeating units of the two-monomer blocks shown as structures II, III and IV, they may comprise a block copolymer, such as when a long chain of the monomer having the n subscript is joined with a long chain of the monomer having the m subscript, they may comprise a random mixture of the individual monomers of the two-monomer blocks shown as structures II, III and IV, or they may comprise solely the monomer having the n subscript, as when m is zero, of the two-monomer blocks shown as structures II, III and IV.

The carboxy starch polymer composition of the present invention may be comprised of random mixtures of the two-monomer blocks shown as structures II-IV. Additionally, the individual monomers containing the m and n subscripts in structures II-IV may be randomly distributed throughout the polymer chain length of the carboxy starch polymers of the present invention.

When the polymer of the present invention is prepared by the methods hereinbefore referenced, and is comprised of a mixture of Tables II-IV, such polymer will typically comprise from about 25% to 100%, more typically from about 50% to about 90%, most typically from about 70% to about 90% of structure II, with the balance being comprised of structures III and IV.

A fourth preferred starch polymer useful in the present invention is of the general formula:

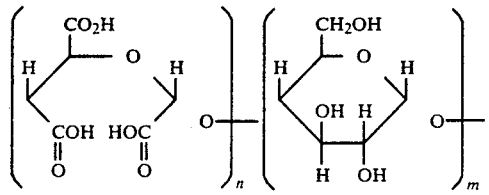

(V)

or the neutralized carboxylic acid salts thereof, wherein n is in the range of from about 5 to about 250, preferably from about 5 to about 150, most preferably from about 5 to about 100, and m is in the range of from 0 to about 250, preferably from 0 to about 150, most preferably from 0 to about 100, provided that the sum of n and m is in the range of from about 5 to about 250, preferably from about 5 to about 150, most preferably from about 5 to about 100. The number average degree of carboxylation of this fourth preferred starch polymer typically ranges from about 1.5 to about 3, preferably from about 2 to about 3, most preferably from about 2.5 to about 3. The mass average molecular weight of this fourth preferred starch polymer typically ranges from about 1,000 to about 50,000, preferably from about 1,000 to about 20,000.

This fourth preferred starch polymer may be prepared as described in U.S. Pat. No. 3,665,000, issued May 23, 1972, to Hills et al., the disclosure of which is incorporated herein by reference.

This fourth preferred starch polymer may comprise repeating units of the two-monomer block shown in structure V, it may comprise a block copolymer, such as when a long chain of the monomer having the n subscript is joined with a long chain of the monomer having the m subscript, it may comprise a random mixture of the individual monomers of the two-monomer block shown in structure V, or it may comprise solely either the monomer having the n subscript, as when m is zero, of the two-monomer block shown in structure V.

Mixtures of the starch polymers of the present invention may be used as the plaque-inhibiting active agent in the compositions of the present invention, including mixtures of the four preferred starch polymers discussed herein. The mass average molecular weight of active agent in such polymer mixture typically ranges from about 1,000 to about 250,000, preferably from about 3,000 to about 200,000, most preferably from about 5,000 to about 100,000. Mixtures of high molecular weight and low molecular weight starch polymer material may be used to achieve a polymer mixture having an appropriate mass average molecular weight. When mixtures of starch polymers are used as the plaque-inhibiting active agent in the compositions of the present invention, the number average degree of carboxylation for the polymer mixture typically ranges from about 1 to about 3, preferably from about 1.5 to about 3, most preferably from about 1.7 to about 2.5.

When the neutralized carboxylic acid salts of the starch polymers useful in the present invention are prepared, one or more of the available carboxylic acid groups on the polymer will be neutralized with alkali metal or quaternary ammonium cations, with alkali metals being preferred, and sodium being most preferred.

The degree of carboxylation of the final carboxy starch product is dependent upon the method of oxidation used, the stoichiometry of the oxidation used, the stoichiometry of the oxidation reaction, and the level of oxidation of the dialdehyde starch starting material. However, achieving the desired degree of carboxylation is well within the ability of one skilled in the art. In general, oxidation using chlorous acid will produce carboxy starch polymers with a degree of carboxylation in the range of from about 1.0 to about 2.0, while dinitrogen tetroxide tends to generate carboxy starches with a degree of carboxylation in the range of from about 1.3 to about 3.0.

The degree of carboxylation in the carboxy starch polymers is determined by potentiometric titration with sodium hydroxide after ion exchange to the free acid form. Carboxy-starches give relatively sharp inflection points in the pH range of 8.0–9.0. Residual alkalinity (assumed to be sodium carbonate) is determined by titration with hydrochloric acid to the phenolphthalein endpoint. Dialdehyde content is determined by a time reaction with sodium hydroxide at 70° C. Moisture is determined by Karl Fischer titration.

The carboxy starch polymer useful in the present invention may optionally be interspersed with non-starch monomers. Preferred are monomers which add additional carboxylate groups to the polymer. Most preferred are acrylic acid and acrylate monomers.

The amount of plaque-inhibiting carboxy starch polymer active agent used in the compositions of the present invention generally ranges from about 0.1% to about 10% by weight, preferably from about 1% to about 8% by weight, most preferably from about 3% to about 5% by weight. For a dentifrice composition, the most preferred concentration of active agent ranges from about 3% to about 5% by weight. For a mouthwash composition, the most preferred concentration of active agent ranges from about 3% to about 5% by weight.

As discussed above, the carboxy starch polymers used in the present invention are useful for inhibiting the formation of plaque on the tooth surface. While not intending to necessarily be limited thereby, it is believed that these plaque-inhibiting carboxy starch polymer active agents are additionally beneficial in that they inhibit plaque formation without discernibly staining the surface of the treated teeth.

Pharmaceutically Acceptable Carrier

The carrier for the calculus- and plaque-inhibiting active agent of the present invention can be any vehicle suitable for use in the oral cavity, including the usual components of mouthwashes, toothpastes, topical dental gels, toothpowders, prophylaxis pastes, lozenges, gums and the like, and are more fully described hereinafter. Dentifrices and mouthwashes are the preferred systems, with toothpastes being the more preferred.

Toothpastes and toothpowders contain as a major component an abrasive. The abrasive polishing material contemplated for use in the present invention can be any material which does not excessively abrade dentin. These include, for example, silicas including gels and precipitates, calcium carbonate, $\beta$-phase calcium pyrophosphate, tricalcium phosphate, calcium polymetaphosphate, insoluble sodium polymetaphosphate, hydrated alumina, and resinous abrasive materials such as particulate condensation products of urea and formaldehyde, and others such as disclosed by Cooley et al., in U.S. Pat. No. 3,070,510, issued Dec. 25, 1962, which is incorporated herein by reference. Mixtures of abrasives may also be used.

Various types of silica dental abrasives can provide the unique benefits of exceptional dental cleaning and polishing performance without unduly abrading tooth enamel or dentin. Silica abrasive materials are also exceptionally compatible with sources of soluble fluoride and other ion sources. For these reasons they are preferred for use herein. Of course the abrasive selected should also exhibit excellent compatibility with soluble strontium ion sources.

The silica abrasive polishing materials useful herein, as well as the other abrasives, generally have an average particle size ranging between about 0.1 and 30 microns, preferably between 5 and 15 microns. The silica abrasive can be precipitated silica or silica gels such as the silica xerogels described in Pader et al., U.S. Pat. No. 3,538,230, issued Mar. 2, 1970 and DiGiulio, U.S. Pat. No. 3,862,307, issued June 21, 1975, both of which are incorporated herein by reference. Preferred are the silica xerogels marketed under the tradename "Syloid" by the W. R. Grace & Company, Davidson Chemical Division. Preferred precipitated silica materials include those marketed by the J. M. Humber Corporation under the tradename "Zeodent", particularly the silica carrying the designation "Zeodent 119". These silica abrasives are described in U.S. Pat. No. 4,340,583, issued July 29, 1982, the disclosure of which is incorporated herein by reference.

The abrasive in the dentifrice compositions described herein is present at a level of from about 6% to about 70%, preferably from about 15% to about 25% when the dentifrice is a toothpaste. Higher levels, as high as 90%, may be used if the composition is a toothpowder.

Another embodiment of the present invention is a mouthwash composition. Conventional mouthwash composition components can comprise the carrier for the actives of the present invention. Mouthwashes generally comprise from about 20:1 to about 2:1 of a water-/ethyl alcohol solution and preferably other ingredients such as flavoring agents, sweeteners, humectants and sudsing agents such as those described above. The humectants, such as glycerin and sorbitol, give a moist feel to the mouth. Generally, on a weight basis the mouthwashes of the invention comprise from about 5% to about 60%, preferably from about 10% to about 25%, of ethyl alcohol; from 0% to about 20%, preferably from about 5% to about 20%, of a humectant; from 0% to about 2%, preferably from about 0.01% to about 0.15%, of an emulsifying agent; from 0% to about 0.5%, preferably from about 0.005% to about 0.06%, of a sweetening agent such as saccharin; from 0% to about 0.3%, preferably from about 0.03% to about 0.3%, of a flavoring agent; and the balance water.

Suitable lozenge and chewing gum components are disclosed in U.S. Pat. No. 4,083,955, issued Apr. 11, 1978 to Grabenstetter et al., which is incorporated herein by reference.

Suitable topical dental gels generally comprise a base of a humectant such as glycerin thickened with a suitable agent. Such gels generally do not contain an abrasive.

In addition to the above-described components, the oral compositions of the present invention may include a number of optional ingredients.

Such optional ingredients include a safe and effective amount of a fluoride ion source, which typically is in the form of a water-soluble fluoride compound. This water-soluble fluoride compound is typically present in the compositions of this invention in an amount sufficient to give a fluoride concentration of from about 0.0025% to about 5.0% by weight, preferably from about 0.005% to about 2.0% by weight. Preferred fluorides are sodium fluoride, stannous fluoride, indium fluoride, acidulated phosphate fluoride and sodium monofluorophosphate. U.S. Pat. No. 2,946,735, issued July 26, 1960 to Norris et al., and U.S. Pat. No. 3,678,154, issued July 18, 1972 to Widder et al., disclose such salts as well as others. The disclosures of these patents are incorporated herein by reference.

Other optional ingredients include pyrophosphate anticalculus agents, e.g., tetrasodium pyrophosphate, tetrapotassium pyrophosphate, and dihydrogen disodium pyrophosphate, which are typically used at the 0.1% to 5% levels. See U.S. Pat. No. 4,885,155, cited above.

Flavoring agents can also be added to the dentifrice and other compositions of the present invention. Suitable flavoring agents include oil of wintergreen, oil of peppermint, oil of spearmint, oil of sassafras and oil of clove. Sweetening agents are also useful and include aspartame, acesulfame, saccharin, dextrose, levulose and sodium cyclamate. Flavoring and sweetening agents are generally used in the compositions herein at levels of from about 0.005% to about 2% by weight.

The compositions of this invention may also contain emulsifying agents. Suitable emulsifying agents are those which are reasonably stable and foam throughout a wide pH range, and include non-soap anionic, non-ionic, cationic, zwitterionic and amphoteric organic synthetic detergents. Many of these suitable surfactants are disclosed by Gieske et al. in U.S. Pat. No. 4,051,234, issued Sept. 27, 1977, which is incorporated herein by reference.

Water may also be present in the compositions of this invention. Water employed in the preparation of commercially suitable compositions should preferably be deionized and free of organic impurities. Water generally comprises from about 10% to about 50% by weight, preferably from about 20% to about 40% by weight, of the toothpaste compositions herein. These amounts of water include the free water which is added plus that which is introduced with other materials, such as with sorbitol.

In preparing toothpastes, it is common to add some thickening material to provide a desirable consistency. Preferred thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as gum karaya, gum arabic and gum tragacanth, and polysaccharide gums such as xanthan gum can also be used. Colloidal magnesium aluminum silicate or finely divided silica can be used as part of the thickening agent to further improve texture. Thickening agents in an amount from about 0.5% to about 5.0% by weight of the total composition may be used.

It is also desirable to include a humectant in a toothpaste to keep it from hardening. Suitable humectants include glycerin, sorbitol and other edible polyhydric alcohols at a level of from about 10% to about 70% by weight.

The pH of the present compositions and/or their pH in the mouth can be any pH which is safe for the mouth's hard and soft tissues. Such pH's are generally from about 3 to about 10, preferably from about 7 to about 9.

In addition to the above-described oral compositions, the present invention also encompasses a method of inhibiting calculus and plaque on treated tooth surfaces. This method involves applying a safe and effective amount of the antiplaque polymer, such as the carboxy starch polymer, and the TMS and/or TDS materials to the tooth surface. The term "safe and effective amount," as used herein for the method of inhibiting plaque, means a sufficient amount, typically about 0.125 grams, preferably about 0.100 grams, most preferably about 0.075 grams, of carboxy starch polymer applied to the oral cavity for inhibiting the formation of plaque in the oral cavity, while being safe to the hard and soft tissues of the oral cavity. The TMS/TDS material is present in amounts typically in the 1,000 ppm–100,000 ppm range, and the teeth are thus "bathed" in the mixed active ingredients. Such an application is typically made by applying the above-described oral compositions to the oral cavity. For example, when the oral composition is a toothpaste, typically 1.5 grams of toothpaste containing 5 wt. % of the carboxy starch polymer and 1%–5% of the TMS/TDS are applied to an applicating device, e.g., a toothbrush. The applicating device is then contacted with the tooth surface in a manner such that the oral composition is contacted with the tooth surface. The applicating device may be further used to effect an even distribution of the oral composition onto said tooth surface, for example by brushing. The brushing will preferably last for a period of 1–3 minutes at least once, preferably three times, daily on a regular basis, although the actual time period of brushing is dependent upon the individual user. Following brushing, the toothpaste residue is typically removed from the tooth surface by using a liquid acceptable to the oral cavity, typically water, to rinse the oral cavity.

When the oral composition is embodied in a mouthwash, typically 10 ml. of liquid mouthwash containing the antiplaque polymer and the TMS/TDS is introduced to the oral cavity. The liquid mouthwash is then agitated, preferably for a period of 2 minutes, within the oral cavity to obtain an improved distribution of the mouthwash over the tooth surface. The actual time of agitation is dependent upon the individual user. Following agitation, the mouthwash is typically expectorated from the oral cavity.

The following illustrate representative oral compositions employing safe and effective amounts of the TMS/TDS/polymers of the present invention, as well as various adjunct oral care ingredients.

EXAMPLE I

This example shows the synthesis of a carboxy starch polymer. The following steps are performed:

A solution containing 90.45 g of $NaClO_2$ in 1 l. $H_2O$ is initially prepared. 28.6 ml of acetic acid and 20.0 g of dialdehyde starch are added, in order, to this initial solution, and the resulting reaction mixture is stirred for 22 hrs. at room temperature. The reaction mixture is then aerated with argon and the pH is adjusted to 8–9 using 50% NaOH solution. The mixture is poured into 1 l. of ethanol, and a solid crude reaction product is isolated by decantation. The reaction product is then dissolved in 200 ml of $H_2O$ to form a second solution. This second solution is poured into 600 ml ethanol, and the solid product is again isolated by filtration, dissolved in $H_2O$, and is then lyophilized to produce 6.33 g of white solid carboxy starch. The degree of carboxylation of the white solid carboxy starch is determined to be approximately 1.7 by potentiometric titration.

EXAMPLE II

The following is a representative example of a toothpaste of the present invention.

| Component | Wt % |
|---|---|
| Sorbitol (70% aqueous solution) | 49.56 |
| Sodium saccharin | 0.30 |
| Dye solution | 0.35 |
| Precipitated silica | 18.00 |
| TMS/TDS (per Reaction B) | 2.0 |
| Sodium fluoride | 0.25 |

| Component | Wt % |
| --- | --- |
| Flavor | 1.30 |
| Sodium alkyl sulfate (27.9% aqueous solution) | 5.00 |
| Carbopol 940S (available from B. F. Goodrich) | 0.20 |
| Xanthan gum | 0.60 |
| Carboxy starch polymer of Example I | 5.00 |
| Distilled water | Balance |

The above composition is made by combining the water, TMS/TDS and part of the sorbitol in an agitated mixture and heating this mixture to 140° F. The carboxy starch polymer, saccharin, sodium fluoride and precipitated silica are then added in order and the total mixture is mixed for from 5 to 10 minutes. The flavor, dye and surfactant are then added. In a separate vessel the remainder of the sorbitol, the Carbopol and the xanthan gum are slurried together and then added to the main mix tank. The complete batch is mixed for about one-half hour and subsequently milled and deaerated.

EXAMPLE III

This example illustrates the preparation of a typical carboxy starch polymer used in this invention.

A reaction vessel is charged with 8.0 parts of corn starch and 400 parts of water at 80° C. The resulting suspension is cooled to 0° to 5° C., whereupon 16.1 parts of sodium metaperiodate are added. The pH of the mixture is adjusted to a level of 5.0 by the addition of sufficient glacial acetic acid and the reaction is allowed to proceed, under agitation, at a temperature of 0° to 5° C. for a period of 42 hours. The reaction mixture is centrifuged and the dialdehydestarch precipitate is then washed with water to remove all traces of inorganic salts.

Thereafter, a reaction vessel fitted with a condenser, a drying tube and means for mechanical agitation, is charged with a solution of 3.8 parts of dinitrogen tetroxide in 250 parts of dry carbon tetrachloride. This solution is vigorously agitated, whereupon 4.0 parts of the above prepared dialdehydestarch is incrementally added thereto. The reaction is allowed to proceed at room temperature for a period of 22 hours. The mixture is then recharged with 3.8 parts of dinitrogen tetroxide and the reaction is allowed to proceed for an additional 48 hours. The excess dinitrogen tetroxide is removed by bubbling nitrogen gas through the system until the red nitrous oxide fumes have substantially disappeared. The white solid product is then filtered, washed with water and dried.

EXAMPLE IV

The following is another representative toothpaste of the present invention.

| Component | Wt % |
| --- | --- |
| Sorbitol (70% aqueous solution) | 50.75 |
| TMS/TDS (per Reaction A) | 1.5 |
| Sodium saccharin | 0.30 |
| Dye solution | 0.35 |
| Precipitated silica | 18.5 |
| Sodium fluoride | 0.25 |
| Flavor | 1.30 |
| Sodium alkyl sulfate (27.9% aqueous solution) | 5.00 |
| Carbopol 940s | 0.20 |
| Xanthan gum | 0.60 |
| Carboxy starch polymer of Example III | 4.15 |

| Component | Wt % |
| --- | --- |
| Distilled water | Balance |

In addition to the levels and combinations of ingredients shown in these examples, others can be used which are consistent with the invention disclosed.

EXAMPLE V

This example illustrates the preparation of a typical carboxy starch polymer used in this invention.

A reaction vessel is charged with 49.1 g of commercial non-defatted cornstarch and 300 mls of water at 25° C. to form a suspension. 71.3 g of unbuffered sodium metaperiodite in 910 ml. of water are added to this suspension to form a reaction mixture. The reaction is allowed to proceed, under agitation, at room temperature for a period of 22 hours. The reaction mixture is filtered and the dialdehyde starch precipitate is then washed with water to remove any traces of inorganic salts.

Thereafter, 45 g of the dialdehyde starch precipitate is charged into an open beaker. 203 g of 1 M $NaClO_2$ and 64 ml. of glacial acetic acid are then added to the open beaker to form a slurried reaction mixture. The oxidation reaction of the dialdehyde starch is allowed to proceed, under agitation, at room temperature for a period of 22 hours. As the reaction progresses, the reaction mixture changes from a light yellow to an orange color with the evolution of a considerable quantity of chlorine dioxide gas. At the conclusion of the reaction nitrogen is bubbled through the reaction mixture to remove all but traces of chlorine dioxide, and the solution is adjusted to a pH ranging from 8 to 9 with 50% NaOH solution.

The oxidized product is precipitated by pouring the reaction mixture, with rapid stirring, into 2 volumes of absolute ethanol, and then filtered. The filtered starches are then reprecipitated in this manner to afford 9.4 g of carboxy starch having a degree of carboxylation of 1.9.

EXAMPLE VI

This example shows a mouthwash composition containing a carboxy starch polymer of the present invention.

The mouth rinse is prepared as follows:

| Component | Wt % |
| --- | --- |
| Carboxy starch polymer of Example V | 4.00 |
| TMS/TDS (per Reaction A) | 1.0 |
| Ethanol | 16.25 |
| Glycerin | 10.00 |
| Nonionic surfactant | 0.12 |
| Benzoic acid | 0.05 |
| Sodium saccharin | 0.05 |
| Flavor | 0.15 |
| Color | 0.04 |
| NaOH (10% Sol.) | 0.15 |
| Distilled water | Balance |

The mouth rinse is prepared by adding each of the ingredients to the distilled water and stirring.

Other representative examples of compositions according to this invention are as follows.

EXAMPLE VII

| EXAMPLE VII  A toothpowder comprises the following ingredients. | |
| --- | --- |
| Ingredient | Percent (wt.) |
| TMS/TDS (per Reaction A) | 7.0 |
| Sodium polystyrenesulfonate* | 1.5 |
| NaF | 0.9 |
| Tetrasodium pyrophosphate | 3.5 |
| Silica xerogel (as "Syloid") | Balance |

*See U.S. Pat. No. 4,428,930.

EXAMPLE VIII

The toothpowder of Example VII is modified by replacing the sodium polystyrenesulfonate with an equivalent amount of the following polymers, respectively: sodium polyvinylphosphonic acid (U.S. Pat. No. 4,528,179); sulfonated vinyl aromatic polymer (U.S. Pat. No. 4,375,461); maleic acid copolymer (U.S. Pat. No. 4,362,173); and the zinc-polymer combinations of U.S. Pat. No. 4,118,474.

While the foregoing illustrates not only the use of the basic compositions of this invention and several embodiments thereof, but also various combinations of the herein-disclosed active ingredients with various adjunct agents for oral care, it is to be understood that such adjunct agents are given by way of exemplification and not by way of limitation. Other adjunct oral care agents can be used in such compositions, including materials such as: the ethylenediamine tetraacetates (EDTA) (EDTA generally at effective levels of 0.1%, or less); peroxides, especially 1% aqueous hydrogen peroxide; sodium tripolyphosphate (STPP), typically at 0.5%–10% levels, and the like.

As noted hereinabove, the compositions and methods herein can be desirably formulated with effective amounts of antibacterial agents, pyrophosphates, zinc citrate, various cations, and the like.

By an "effective amount" of an antibacterial agent herein is meant sufficient antibacterial to provide an antiplaque benefit for the compositions. Typically, from about 0.001% to about 1% by weight of the compositions can comprise the desired antibacterial (antiplaque) amount. Preferred antibacterial agents for use herein include, for example, TRICLOSAN, CPC (cetyl pyridinium chloride), PAM (magnesium monoperphthalate; see U.S. Pat. No. 4,670,252), TDEPC (N-tetradecyl-4-ethylpyridinium chloride) and sodium peroxide; TRICLOSAN is especially preferred.

By an "effective amount" of a source of pyrophosphate ions in the compositions herein is meant an amount which will provide adjunct anticalculus benefits, in addition to those provided by the TMS and TDS anions. As noted above, such compositions will comprise from about 0.1% to about 10%, typically 0.1% to 5%, by weight of pyrophosphate ions, which, as noted above, can be sourced from pyrophosphate salt such as tetrasodium, tetrapotassium, and disodium dihydrogen pyrophosphates.

By an "effective amount" of zinc citrate herein is meant an amount sufficient to provide adjunct anticalculus benefits in addition to those provided by the TMS and TDS anions. Typically, an amount of zinc citrate of from about 0.1% to about 5% by weight of the compositions herein is sufficient.

By an "effective amount" of a source of cation, especially cations selected from zinc, indium, strontium and stannous cations, and mixtures thereof, herein is meant a sufficient amount of said cations to provide the benefits which are normally associated with the use of these particular materials in oral compositions. For example, the stannous cation has been associated with an anticaries benefit, as has the indium cation. Zinc and strontium cations have been noted for use in, for example, dentifrice compositions which are used in situations where the teeth have been made "sensitive" to pain, particularly in older teeth which have undergone serious erosion of the dental enamel. Typical usage levels to provide the aforesaid effective amount of such cations generally ranges from about 0.01% to about 3% by weight of the compositions. Materials such as indium chloride, stannous fluoride, strontium chloride, zinc chloride, and the like can be used for such purposes.

By an "effective amount" of sodium nitrate and potassium nitrate (preferred) herein is meant sufficient amounts of such materials to provide desensitization of otherwise sensitive teeth (as noted above). Typically, such amounts will comprise from about 0.01% to about 5% of the compositions herein.

Additional embodiments of the present invention are illustrated by the following examples.

EXAMPLE IX

A mouthwash base composition comprising water, 15% ethanol, 0.2% flavorants and 0.02% dye is prepared. To this base composition are added the following ingredients to provide Compositions A, B and C.

| Ingredient | | % in Final Composition |
| --- | --- | --- |
| A | TDS | 2.0 |
| | GANTREZ AN | 0.8 |
| | CPC | 0.1 |
| B | TMS | 5.0 |
| | Starch polymer of Example I | 0.3 |
| | H$_2$O$_2$ | 0.9 |
| C | TMS/TDS (40:60 mixture) | 1.0 |
| | Na monofluorophosphate | 0.1 |
| | Starch polymer of Example I | 0.5 |
| | GANTREZ AN | 0.3 |
| | TRICLOSAN | 0.1 |
| | STPP | 3.0 |

EXAMPLE X

A base toothpowder composition comprising 95% Syloid abrasive, 0.5% sodium alkyl sulfate, 0.3% flavorant and 4.2% of a 40:60 TMS/TDS mixture is prepared. To this base composition are added the following ingredients to provide Compositions A, B and C.

| Ingredient | | % in Final Composition |
| --- | --- | --- |
| A | Starch polymer of Example III | 5.0 |
| | NaNO$_3$ | 1.0 |
| | In Cl$_3$ | 0.9 |
| | PAM | 1.0 |
| B | GANTREZ AN | 3.0 |
| | TRICLOSAN | 0.2 |
| | CPC | 0.1 |
| | PAM | 0.3 |
| C | GANTREZ AN | 3.0 |
| | Zn Cl$_2$ | 0.1 |
| | EDTA | 0.05 |
| | STPP | 3.0 |

EXAMPLE XI

A chewing gum comprises 93% standard chewing gum base (chicle), 3% TDS and 5% of the carboxy starch polymer of Example I.

EXAMPLE XII

A lozenge comprising 80% maltose, 10% TDS, 3% of a 1:1 (wt.) mixture of the carboxy starch polymers of Examples I and V, 1% sodium monofluorophosphate 1.5% gum arabic, 0.1% strontium chloride, 0.1% flavorant, 0.05% magnesium stearate (tableting aid), the balance comprising corn starch, is prepared in a standard tablet press. In use, the lozenge is allowed to dissolve slowly in the mouth to bathe the teeth in the combination of active ingredients.

As can be seen from the foregoing, a wide variety of compositions useful for treating teeth in patients who are susceptible to dental calculus and plaque formation and in need of such treatment are provided by the present invention. It will also be appreciated that "multiple" compositions can be used in conjunction with each other, e.g., a toothpaste comprising TMS/TDS/polymer plus a separate toothpaste or mouthwash comprising pyrophosphate, can be separately applied to the teeth, followed by a mouthrinse using, for example, TRICLOSAN, to afford multiple benefits. Such separate usage would not depart from the spirit and scope of this invention.

What is claimed is:

1. An oral care composition, comprising:
   a) an effective amount of an anticalculus agent which is a member selected from the group consisting of the acid or salt form of tartrate monosuccinate, tartrate disuccinate, and mixtures thereof;
   b) an effective amount of a plaque-inhibiting polymer; and
   c) a toxicologically acceptable oral carrier.

2. An oral care composition according to claim 1 comprising at least about 0.1% by weight of said anticalculus agent.

3. An oral care composition according to claim 2 comprising from about 1% to about 15% by weight of said anticalculus agent.

4. An oral care composition according to claim 1 wherein said anticalculus agent is a mixture of said tartrate monosuccinate and tartrate disuccinate at a weight ratio of tartrate monosuccinate: tartrate disuccinate from about 20:80 to about 80:20.

5. An oral care composition according to claim 4 wherein said anticalculus agent comprises a mixture of tartrate monosuccinate and tartrate disuccinate at a weight ratio of about 40:60 of tartrate monosuccinate:-tartrate disuccinate.

6. An oral care composition according to claim 1 wherein said plaque-inhibiting polymer is a member selected- from the group consisting of carboxy starch polymers, acrylic acid polymers, phosphoric acid polymers, maleic acid polymers, sulfonated polymers and modified forms of these polymers, and mixtures thereof.

7. An oral care composition according to claim 6 which comprises at least about 0.1% by weight of said polymer.

8. An oral care composition according to claim 7 wherein the oral carrier comprises a dentifrice, mouthwash, lozenge or chewing gum.

9. An oral care composition according to claim 1, comprising an effective amount of an oral care adjuvant which is a member selected from the group consisting of:
   i) fluoride ion sources;
   ii) antibacterial agents;
   iii) sodium and potassium nitrates;
   iv) sources of zinc, indium, strontium or stannous cations;
   v) peroxides;
   vi) chelants and sequestrants selected from phosphates, and EDTA; and
   vii) mixtures of adjuvants i through vi.

10. An oral care composition according to claim 9 wherein the fluoride ion source is selected from sodium fluoride, sodium monofluorophosphate and stannous fluoride.

11. An oral care composition according to claim 9 wherein the antibacterial agent is 5-chloro-2-(2,4-dichlorophenoxyphenol.

12. A method for preventing the accumulation of calculus on dental enamel while concurrently inhibiting plaque formation on said enamel, comprising contacting said enamel with a safe and effective amount of a composition according to claim 1.

* * * * *